US010117818B2

(12) United States Patent
Lou et al.

(10) Patent No.: US 10,117,818 B2
(45) Date of Patent: Nov. 6, 2018

(54) WET WIPE CONCENTRATE COMPRISING A POLYGLYCERYL FATTY ESTER

(71) Applicant: Arch Personal Care Products, LP, South Plainfield, NJ (US)

(72) Inventors: Khat Kevin Lou, Allendale, NJ (US); Mark Garrison, Allendale, NJ (US); Joseph Librizzi, Allendale, NJ (US)

(73) Assignee: ARCH PERSONAL CARE PRODUCTS, LP, South Plainfield, NJ (US)

( * ) Notice: Subject to any disclaimer, the term of this patent is extended or adjusted under 35 U.S.C. 154(b) by 0 days.

(21) Appl. No.: 15/236,737

(22) Filed: Aug. 15, 2016

(65) Prior Publication Data

US 2017/0042779 A1  Feb. 16, 2017

Related U.S. Application Data

(60) Provisional application No. 62/204,801, filed on Aug. 13, 2015.

(51) Int. Cl.
| *A61K 8/37*   | (2006.01) |
| *C11D 17/04*  | (2006.01) |
| *A61K 8/34*   | (2006.01) |
| *A61Q 1/14*   | (2006.01) |
| *A61Q 19/00*  | (2006.01) |
| *A61K 8/02*   | (2006.01) |
| *A47K 7/03*   | (2006.01) |
| *A61Q 19/10*  | (2006.01) |

(52) U.S. Cl.
CPC ............... *A61K 8/375* (2013.01); *A47K 7/03* (2013.01); *A61K 8/0208* (2013.01); *A61K 8/342* (2013.01); *A61K 8/345* (2013.01); *A61K 8/37* (2013.01); *A61Q 1/14* (2013.01); *A61Q 19/00* (2013.01); *A61Q 19/005* (2013.01); *A61Q 19/10* (2013.01); *C11D 17/041* (2013.01); *A61K 2800/30* (2013.01); *A61K 2800/56* (2013.01); *A61K 2800/5922* (2013.01); *A61K 2800/87* (2013.01)

(58) Field of Classification Search
CPC .......... A61K 8/375; A61K 8/345; A61K 8/37; A61K 8/0208; A61K 8/342; A61Q 1/14; A61Q 19/00; A61Q 19/005; A61Q 19/10; C11D 17/041
See application file for complete search history.

(56) References Cited

U.S. PATENT DOCUMENTS

| 6,280,712 B1* | 8/2001 | Ansmann .................. A61K 8/27 424/400 |
| 2005/0025957 A1* | 2/2005 | Issberner ............. A61K 8/0208 428/321.1 |
| 2005/0037042 A1* | 2/2005 | Tom Dieck ............ A61K 8/345 424/401 |
| 2007/0196289 A1* | 8/2007 | Blatt ....................... A61K 8/35 424/59 |
| 2007/0248632 A1 | 10/2007 | Goget et al. |
| 2009/0131542 A1* | 5/2009 | Issberner ............. A61K 8/0208 514/777 |
| 2010/0278882 A1* | 11/2010 | Liebmann ............ A61K 8/0241 424/401 |
| 2010/0298432 A1* | 11/2010 | Ansmann ............. A61K 8/0208 514/552 |
| 2011/0287073 A1 | 11/2011 | Strauss et al. |
| 2012/0027826 A1 | 2/2012 | Strauss et al. |
| 2014/0140940 A1* | 5/2014 | Von Thaden .......... A61Q 17/04 424/60 |
| 2015/0064119 A1* | 3/2015 | Henrike .................. A61K 8/24 424/59 |
| 2015/0141522 A1* | 5/2015 | Kruse ..................... A61K 8/34 514/685 |

FOREIGN PATENT DOCUMENTS

| DE | 102004031550 A1 | 2/2006 |
| EP | 1891935 A1 | 2/2008 |
| EP | 2206489 A1 | 7/2010 |

OTHER PUBLICATIONS

Database GNPD [Online] Mintel; "Cleansing Balm," Database accession No. 1349641, Jun. 30, 2010, XP002761467, 3 pgs.*
Database GNPD [Online] Mintel; "Cleansing Balm," Database accession No. 1349641, Jun. 30, 2010, XP002761467, (3 pgs.).
Database GNPD [Online] Mintel; "Facial Cleansing Towelettes," Database accession No. 3174905, Jun. 30, 2015, XP002761468, (3 pgs.).
Database GNPD [Online] Mintel; "3 in 1 Cleansing Wipes," Database accession No. 1788484, May 31, 2012, XP002761469, (3 pgs.).
Database GNPD [Online] Mintel; "Express Cleansing Wipes," Database accession No. 2975705, Feb. 28, 2015, XP002761470, (2 pgs.).
International Search Report and Written Opinion for the corresponding PCT Application No. PCT/EP2016/069355, filed Aug. 15, 2016 (14 Pages).

* cited by examiner

*Primary Examiner* — Charles I Boyer
(74) *Attorney, Agent, or Firm* — Lucas & Mercanti LLP

(57) ABSTRACT

The present invention relates to a wet wipe concentrate composition which may be blended with water or another solvent to form an impregnating formulation for a wet wipe. The present invention also relates to said wet wipe impregnating formulation and a wet wipe containing said formulation.

13 Claims, No Drawings

WET WIPE CONCENTRATE COMPRISING A POLYGLYCERYL FATTY ESTER

RELATED APPLICATIONS

The present application is based on and claims priority to U.S. Provisional Patent application Ser. No. 62/204,801, filed on Aug. 13, 2015, which is incorporated herein by reference in its entirety.

FIELD OF INVENTION

The present invention relates to a wet wipe concentrate composition which may be blended with water or another solvent to form an impregnating formulation for a wet wipe. The present invention also relates to said wet wipe impregnating formulation and a wet wipe comprising a wipe substrate and the wet wipe impregnating formulation.

BACKGROUND OF THE INVENTION

Wet wipe concentrates are available on the market. However, these concentrates often contain water in significant amounts which require that preservatives be added to the concentrate. The problem with adding a preservative to the concentrate, is that the final end use of the concentrate may be limited and most preservatives are viewed negatively. But a concentrate that does not require a preservative allows the flexibility for the wet wipe manufacturer to add any preservative they wish to, based on the particular end customer. Further, the presence of water makes the concentrate less cost effective i.e., less concentrated).

Also many of the concentrates available are generally hazy. This haze is a sign of instability in the concentrate, i.e., it can mean the concentrate will have a short shelf life on storage and separate There is a need in the art to provide a wet wipe concentrate that is highly dilutable, preservative free so that the end use of the concentrate is not limited, is highly stable during storage prior to use, and is essentially clear. The present invention provides an answer to that need.

SUMMARY OF THE INVENTION

In one aspect, the present invention provides a concentrate for impregnating, i.e., saturating, a wet wipe, when diluted, the concentrate composition containing (a) an emulsifier having an HLB between 8 and 16; (b) a humectant; and (c) an emollient. As used herein, "HLB" is the abbreviation for "hydrophilic lipophilic balance". Said value expresses the water and oil solubility of, in particular non-ionic, emulsifiers, i.e., expresses the lipophilic and hydrophilic properties of an emulsifier, which are determined by the different parts of the emulsifier molecules. The higher the HLB value of an emulsifier, the more hydrophilic and water soluble it is. According to the method of Griffin, the HLB value of an emulsifier molecule is calculated as follows:

$$HLB = 20 \times \text{molecular weight(hydrophilic part)/molecular weight(whole molecule)}$$

The hydrophilic part of an emulsifier molecule may e.g., be the polyglyceryl or ethoxylate part of a polyglyceryl fatty ester, ethoxylated fatty alcohol or an ethoxylated fatty acid. When the molecular weight of the hydrophilic part and/or the whole molecule differs within an emulsifier, the HLB is calculated as an average of the HLB's of the emulsifier.

In a further aspect, provided is a wet wipe impregnating formulation, i.e., a wet wipe saturating formulation, comprising the concentrate composition described herein and a fluid, wherein the fluid is water, a lower alcohol or a mixture thereof. As used herein, "lower alcohol" means a straight or branched hydrocarbon chain having 2 to 4 carbon atoms and at least one hydroxyl groups, wherein the hydrocarbon chain may optionally comprise one or several heteroatoms such as e.g., oxygen or sulfur.

In an additional aspect, provided is a wet wipe comprising a wipe substrate impregnated, i.e., saturated, with the wet wipe impregnating formulation.

These and other aspects will become apparent when reading the detailed description of the invention.

DETAILED DESCRIPTION OF THE EMBODIMENTS

The concentrate composition for use in wet wipes of the present invention contains a) an emulsifier having an HLB between 8 and 16, b) a humectant; and c) an emollient. Optionally, the concentrate may contain a small amount of water.

Suitable emulsifiers useable as component (a) include for example polyglyceryl fatty esters, ethoxylated fatty alcohols, ethoxylated fatty acids, ethoxylated sorbitan esters, in particular fatty esters of ethoxylated sorbitan, and a mixture thereof. The term "fatty", as used herein, means a hydrocarbon chain having 4 to 36 carbon atoms, typically 8 to 28 carbon atoms, and in particular 12 to 22 carbon atoms. The chain may be straight or branched and may be saturated or unsaturated, which typically means one or two double bonds in the chain. The term "ethoxylate", as used herein, means an ether produced by addition of one or more molecules of ethylene oxide, wherein an ethoxylate chain typically is built up from 4 to 10 ethylene oxide units. Ethoxylated fatty alcohols includes, for example, Steareth-20. Ethoxylated fatty acids include, for example, PEG-100 Stearate, Ethoxylated sorbitan esters include, for example, Polysorbate 20. Other ethoxylated fatty alcohols, ethoxylate fatty acids and ethoxylated sorbitan esters may be used without departing from the present invention.

In one embodiment, the emulsifier comprises a polyglyceryl fatty ester. Polyglyceryl fatty esters are formed by esterification of fatty acids to one or several hydroxyl groups of polyglycerols, wherein the fatty acids generally are saturated or mono-unsaturated fatty acids. As glycerol is a trifunctional molecule, it may condense with itself to give polymers. These polyglycerols are hydroxy-containing ethers, with diglycerol being the simplest example.

The polyglycerol components of said polyglyceryl fatty esters generally are built up from 2 molecules to 12 molecules of glycerin, more typically from 3 to 10 molecules of glycerin, based on an average.

The saturated fatty acid components of said polyglyceryl fatty esters include caprylic acid, capric acid, lauric acid, myristic acid, palmitic acid, stearic acid, arachidic acid, behenic acid, lignoceric acid, cerotic acid and mixtures thereof. The mono-unsaturated fatty acid components of said polyglyceryl fatty esters include oleic acid, decaoleic acid and mixtures thereof.

The polyglyceryl fatty ester may e.g., comprise polyglyceryl monodecaoleate such as polyglyceryl-10 decaoleate; polyglyceryl monooleate such as polyglyceryl-2-monooleate, polyglyceryl-3 monooleate, polyglyceryl-4 monooleate, polyglyceryl-6 monooleate, or polyglyceryl-10 monooleate; polyglyceryl dioleate such as polyglyceryl-2 dioleate, polyglyceryl-3 dioleate, polyglyceryl-5 dioleate, polyglyceryl-6 dioleate or polyglyceryl-10 dioleate; polyglyceryl trioleate such as polyglyceryl-5 trioleate or polyglyceryl-10 trioleate; polyglyceryl tetraoleate such as polyglyceryl-2 tetraoleate, polyglyceryl-6 tetraoleate, or polyglyceryl-10 tetraoleate; polyglyceryl pentaoleate such as polyglyceryl-4 pentaoleate, polyglyceryl-6 pentaoleate, or polyglyceryl-10 pentaoleate; polyglyceryl heptaoleate such as polyglyceryl-6 heptaoleate, polyglyceryl-10 heptaoleate; polyglyceryl monostearate such as polyglyceryl-2 monostearate, polyglyceryl-3 monostearate, polyglyceryl-4 monostearate, polyglyceryl-5 monostearate, polyglyceryl-6 monostearate or polyglyceryl-10 monostearate; polyglyceryl distearate such as polyglyceryl-2 distearate, polyglyceryl-3 distearate, polyglyceryl-4 distearate, polyglyceryl-6 distearate, or polyglyceryl-10 distearate; polyglyceryl tristearate such as polyglyceryl-4 tristearate, polyglyceryl-5 tristearate, polyglyceryl-6 tristearate, or polyglyceryl-10 tristearate; polyglyceryl tetrastea rate such as polyglyceryl-2 tetrastearate; polyglyceryl pentastearate such as polyglyceryl-4 pentastearate, polyglyceryl-6 pentastearate, or polyglyceryl-10 pentastearate; polyglyceryl heptastearate such as polyglyceryl-10 heptastearate; polyglyceryl isostearate such as polyglyceryl-2 isostearate, polyglyceryl-3 isostearate, polyglyceryl-4 isostearate, polyglyceryl-6 isostearate, or polyglyceryl-10 isostearate; polyglyceryl diisostearate such as polyglyceryl-2 diisostearate, polyglyceryl-3 diisostearate, polyglyceryl-4 diisostearate, polyglyceryl-6 diisostearate, polyglyceryl-10 diisostearate, or polyglyceryl-15 diisostearate; polyglyceryl triisostearate such as polyglyceryl-2 triisostearate, polyglyceryl-3 triisostearate, polyglyceryl-5 triisostearate, polyglyceryl-10 triisostearate; polyglyceryl tetraisostearate such as polyglyceryl-2 tetraisostearate; polyglyceryl caprylate such as polyglyceryl-2 caprylate, polyglyceryl-3 caprylate, polyglyceryl-4 caprylate, polyglyceryl-6 caprylate, or polyglyceryl-10 caprylate; polyglyceryl dicaprylate such as polyglyceryl-5 dicaprylate; polyglyceryl sesquicaprylate such as polyglyceryl-2 sesquicaprylate; polyglyceryl octacaprylate such as polyglyceryl-6 octacaprylate; polyglyceryl caprate such as polyglyceryl-2 caprate, polyglyceryl-3 caprate, polyglyceryl-4 caprate, polyglyceryl-5 caprate, polyglyceryl-6 caprate, polyglyceryl-10 caprate; polyglyceryl dicaprate such as polyglyceryl-3 dicaprate or polyglyceryl-6 dicaprate; polyglyceryl caprylate/caprate such as polyglyceryl-4 capyrlateicaprate, polyglyceryl-6 caprylate/caprate, or polyglyceryl-10 caprylate/caprate; polyglyceryl palmitate such as polyglyceryl-2 palmitate, polyglyceryl-3 palmitate, polyglyceryl-6 palmitate or polyglyceryl-10 palmitate; polyglyceryl dipalmitate such as polyglyceryl-6 dipalmitate or polyglyceryl-10 dipalmitate; polyglyceryl tetrabehenate such as polyglyceryl-6 tetrabehenate; polyglyceryl myristate such as polyglyceryl-6 myristate or polyglyceryl-10 myristate; polyglyceryl rincinoleate such polyglyceryl-6 polyricinoleate or polyglyceryl-10 ricinoleate; or mixtures thereof. Polyglyceryl-10 oleate is generally used.

In a further embodiment, the emulsifier is an ethoxylated fatty alcohol. The ethoxylated fatty alcohol may be derived from any fatty alcohol having a carbon chain length of from 4 carbon atoms to 36 carbon atoms, generally from 6 carbon atoms to 28 carbon atoms, such as from 12 carbon atoms to 22 carbon atoms. In one embodiment, the fatty alcohol may comprise a mixture of fatty alcohols. Examples of fatty alcohols include cetyl alcohol, stearyl alcohol, lauryl alcohol, myristyl alcohol, behenyl alcohol and mixtures thereof.

Generally, the emulsifier is present in an amount between 15% and 60% by weight, typically between 20% and 50% by weight, more typically between 20% and 40% by weight, based on the weight of the composition.

Suitable humectants useable as component (b) are typically humectants that do not cloud or discolor the concentrate. Examples of humectants include amino acids, pyrrolidone carboxylic acid, lactic acid and salts thereof, lactitol, urea and urea derivatives such as e.g., hydroxyethyl urea, uric acid, glucosamine, creatinine, cleavage products of collagen, chitosan and chitosan salts/derivatives such as e.g., chitosan ascorbate, and, in particular, polyols. According to the invention, polyols are organic compounds that comprise at least two hydroxyl groups. Generally, the polyol is a straight or branched hydrocarbon chain having at least two hydroxyl groups, wherein the hydrocarbon chain may optionally comprise one or several heteroatoms such as e.g., oxygen or sulfur. The polyol may for example be glycerol, polyglyerin, such as diglycerol, triglycerol or polyglycerin-6, ethylene glycol, propylene glycol, butylene glycol, erythritol, 1,2,6-hexanetriol, polyethylene glycols, sugars and sugar derivatives (e.g., fructose, glucose, maltose, maltitol, mannitol, inositol, sorbitol, sorbityl silanediol, sucrose, trehalose, xylose, xylitol, glucuronic acid and salts thereof), ethoxylated sorbitol (Sorbeth-6, Sorbeth-20, Sorbeth-30, Sorbeth-40), honey and hydrogenated honey (as used herein, "hydrogenated honey" is the end product of controlled hydrogenation of honey), hydrogenated starch hydrolyzates and mixtures of hydrogenated wheat protein and PEG-20-acetate copolymer. According to one particular embodiment of the present invention, the humectant is a polyol, in particular propylene glycol, glycerol, diglycerol and/or triglycerol. Glycerol is generally used in the present concentrate.

The humectant is generally present in an amount between 15% and 45% by weight, and more typically between 20% and 40% by weight, based on the weight of the composition.

Suitable emollients useable as component (c) of the composition according to the invention include oils. As used herein, "oil" means an organic compound which at 20° C. is both liquid and water-insoluble. In the context of the invention, insolubility in water is understood to be a solubility of less than 10% by weight at 20° C. Typically, the solubility of less than 1% by weight, more particularly less than 0.1% by weight, in particular less than 0.01% by weight. The oil may e.g., comprise an ester oil, an ether oil or a mixture thereof. As used herein, the term "ester oil" means an oil as above-defined, which comprises at least one ester group. This means that also esters of carbonic acids are ester oils according to the invention. Further, as used herein, the term "ether oil" means an oil as above-defined, which comprises at least one ether group.

Oil components usable in accordance with the invention include, for example, glycerides such as e.g., triglycerides, hydrocarbons such as e.g., petrolatum, silicone oils such as e.g., dimethicone, dialkyl ethers, alkyl esters, dialkyl carbonates and natural oils such as vegetable oils. In dialkyl ethers, alkyl esters and dialkyl carbonates, the alkyl groups may be straight or branched and independently from each other typically have 2 to 16 carbon atoms. Generally, at least one of said alkyl groups has at least 6 carbon atoms, typically at least 8 carbon atoms. A particular dialkyl ether is dicaprylyl ether. As alkyl ester, $C_{12}$-$C_{15}$ alkyl benzoates may be used. Typically dialkyl carbonates are dicaprylyl carbonate, ethylhexyl carbonate, dihexyl carbonate and a mixture thereof, wherein dicaprylyl carbonate is generally used.

Optionally the oil may be an oil that has further functions such as an oil soluble sunscreen. Mixtures of oil components may also be used. According to one particular embodiment of the present invention, the oil is a dialkyl carbonate, such as dicaprylyl carbonate, ethylhexyl carbonate, dihexyl carbonate or a mixture thereof. Dicaprylyl carbonate is typically used in the present concentrate.

In the concentrate composition, the emollient is generally present in an amount between 15% and 60% by weight, based on the weight of the composition, more typically in an amount between 20% and 55% by weight, in particular in an amount between 30% and 55% by weight, based on the weight of the composition.

The concentrate composition may contain other ingredients. However, it is generally preferred that the concentrate is free of preservatives and other ingredients such as fragrances. That way, the concentrate composition can be used in a wide range of wet wipe impregnating formulations, without concern that the preservatives or fragrances are not acceptable for an intended use. In one embodiment, the concentrate composition may contain a small amount of water. Generally, when present, the water will be present in an amount of less than 10% by weight of the composition, typically of less than 7%, for example between 0% and 7%. The amount of water present in the concentrate is enough to require a preservative.

The concentrate compositions of the present invention are produced by mixing the emulsifier, the humectant, the emollient and optionally the further ingredients in an appropriate order, optionally at increased temperatures such as e.g., 25 to 80° C. For example, if polyglyceryl-10 oleate, glycerin and dicaprylyl carbonate are used as emulsifier, humectant and emollient, polyglyceryl-10 oleate and glycerin may be mixed at a temperature between 25° C. and 75° C. first, and the resulting mixture is subsequently mixed with dicaprylyl carbonate of between 25° C. to 75° C. Finally, a small amount of water may optionally be added.

The concentrate composition of the present invention may be used as the base composition to form a wet wipe impregnating formulation, i.e., a wet wipe saturating formulation. For this purpose, said composition is diluted with another fluid. The resulting wet wipe impregnating formulation of the present invention subsequently may be used to impregnate, i.e., saturate, a wipe substrate. Next to this, said wet wipe impregnating formulation can e.g., be used as such as a general skin cleanser or can be used in the production of suncare, e.g., sprayable sunscreen, facial toner, or hair care, e.g., sprayable styling.

As aforementioned, the wet wipe impregnating formulation of the present invention is a mixture of the concentrate composition with another fluid. The fluid mixed with the concentrate composition comprises water, a lower alcohol or a mixture thereof, and typically is water. Lower alcohols include ethanol, isopropyl alcohol, glycols such as e.g., butylene glycol and mixtures thereof. Such a wet wipe impregnating formulation typically contains 0.1% to 50% by weight of the concentrate composition and from 99.9% to 50% by weight of water, a lower alcohol or a mixture thereof, based on the weight of the formulation, and generally contains 0.1% to 30% by weight of the concentrate composition and from 99.9% to 70% by weight of water, a lower alcohol or a mixture thereof, based on the weight of the formulation and typically contains 0.1% to 20% by weight of the concentrate composition and from 99.9% to 80% by weight of water, a lower alcohol or a mixture thereof, based on the weight of the formulation. More typically, the wet wipe impregnating formulation contains between 0.5% and 5% by weight of the concentrate composition and between 99.5 and 95% of water, a lower alcohol or a mixture thereof. Even more typically, the wet wipe impregnating formulation contains between 1.5% and 2.5% by weight of the concentrate composition and between 98.5% and 97.5% of water, a lower alcohol or a mixture thereof, based on the weight of the formulation. Mixing water with the concentrate composition may lead to a wet wipe impregnating formulation in form of an emulsion, typically an oil-in-water emulsion. The emulsion may be a nanoemulsion. Such a nanoemulsion is characterized by (oil) droplets having a particle diameter of less than 200 nm in average, as measured by dynamic light scattering.

As above-mentioned, the wet wipe impregnating formulation of the present invention is in particular used to impregnate into the substrate of a wipe, which results in the wet wipe of the present invention. When the wet wipe impregnating formulation is formed, preservative, fragrances, active pharmaceutical ingredients and/or other additives may optionally be added, so that the fluid expressed from a wet wipe being impregnated with the wet wipe impregnating formulation will be suitable for its intended purposes. The wet wipe impregnating formulations of the present invention may e.g., be used in the production of personal care wipes, such as skin cleansing wipes, baby wipes, or makeup remover wipes. When salicylic acid is used as active pharmaceutical ingredient in a wet wipe impregnating formulation, such a formulation may be used in the production of wipes for anti-acne applications. When antimicrobial agents are used in a wet wipe impregnating formulation, such a formulation may be used in the production of wipes killing germs, such as disinfecting and/or sanitizing wipes In a particular embodiment, the wipe is a single use wipe that is impregnated with the wet wipe impregnating formulation and is stored in a container that will dispense the wipe to a user. The container with the wipes may contain a single wipe, or several wipes.

Suitable containers include a pouch that may contain a single wipe, such as a moist towelette, wherein the pouch is torn open by the user, or may be a pouch with a resealable opening that may contain several wipes in a stacked fashion, a rolled fashion or other suitable formation, wherein the pouch would allow a single wipe to be removed from the opening at a time. Pouches are generally prepared from a fluid impervious material such as a polymer film, a coated paper or a foil such as e.g., an aluminum foil.

Another way to dispense wet wipes of the present invention is to place the wipe in to a fluid impervious container having an opening to access the wipes in the container. Containers may be molded plastic container with lids that are also fluid impervious. Generally, the lid will have an opening to access the wipes in the container.

The wipes in the container may be interleaved or stacked, such that as a wipe is removed from the container the next wipe is positioned in the opening of the container ready for the user to remove the next wipe. Alternatively, each wipe may be part of a strand of material which is perforated between the individual wipes of the strand of material. The continuous wipe material with perforations may be in a folded form or may be in a rolled form. Generally, in the rolled form, the wipe material is fed from the center of the rolled material. As with the interleaved stack, as a wipe is removed from the container, the next wipe is positioned in the opening for the use to remove the next wipe, when needed.

The wet wipe impregnating formulation is impregnated into the wipe substrate such that the wipe is pre-moistened and will express or release the formulation on to a surface as the wipe is run across the surface. Generally, the formulation is saturated into the wipe such that the wipe will release the formulation to the substrate of a surface through the wiping action. The amount of the wet wipe impregnating formulation used to impregnate a wipe substrate may vary over a wide range, depending on the particular wipe substrate and the wipe's intended use. Generally, when impregnating a wipe substrate with the wet wipe impregnating formulation of the present invention, the formulation and the substrate are used in the weight ratio of 10:1 to 1:1, typically 9:1 to 2:1, more typically of 8:1 to 3:1, such as 6:1 to 4:1.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a polymer film as well. The fibers used to prepare a nonwoven wipe substrate may e.g., be cellulosic fibers, thermoplastic fibers and mixtures thereof. The fibers may also be continuous fibers, discontinuous fibers, staple fibers and mixtures thereof. Masses per area of a nonwoven web may vary from 12 grams per square meter to 200 grams per square meter.

The present invention is further described in detail by means of the following Examples. An parts and percentages are by weight and all temperatures are degrees Celsius unless explicitly stated otherwise.

EXAMPLES

Six samples of the concentrate composition were prepared in the proportions shown in Table 1. Each sample was prepared by mixing the polyglyceryl-10 oleate with glycerin in a first beaker and heating the mixture to a temperature between 60° C. and 70° C. In a second beaker dicaprylyl carbonate was slowly heated to a temperature between 60° C. to 70° C. and then slowly added to the first beaker with adequate mixing. In samples 4 and 6, 5 weight percent water was added to the mixture. Samples 1, 2, 3 and 5 did not contain any additional water. After the mixtures were prepared, they were stability tested by heating and cooling the mixtures to the temperatures shown in Table 1. As can be seen, the concentrates were stable between 4° C. and 45° C., remaining clear and not separating.

Each concentrate composition was blended with water such that the resulting impregnating formulations contain 2% by weight of the concentrate composition and 98% by weight water. The mixtures were shaken or stirred to mix the components. After mixing, the mixtures were observed to be oil-in-water emulsions, more precisely oil-in-water nanoemulsions, as determined by dynamic light scattering.

TABLE 1

| Sample No. | Proportion in the concentrate (%) (water unconsidered, if any) | | | Appearance of the concentrate (Stability) | | | Initial pH (2% in 98% water) | Initial particle size (2% in 98% water) |
| --- | --- | --- | --- | --- | --- | --- | --- | --- |
| | Polyglyceryl 10-Oleate | Glycerin | Dicaprylyl Carbonate | RT (25° C.) | 45° C. | 4° C. | | |
| 1 | 20 | 30 | 50 | clear | clear | clear | 7.23 | 91 nm |
| 2 | 33.33 | 33.33 | 33.34 | clear | clear | clear | 7.45 | 97 nm |
| 3 | 25 | 20 | 55 | clear | clear | clear | 6.96 | 78 nm |
| 4 | 30 | 30 | 40 | clear | clear | clear | 7.31 | 65 nm |
| 5 | 40 | 20 | 40 | clear | clear | clear | 7.94 | 68 nm |
| 6 | 20 | 40 | 40 | dear | clear | clear | 7.93 | 77 nm |

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A concentrate composition for use in wet wipes comprising
    (a) an emulsifier having an HLB between 8 and 16;
    (b) a humectant; and
    (c) an emollient,
    wherein:
        the emulsifier comprises a polyglyceryl fatty ester selected from the group consisting of polyglyceryl-10 decaoleate, polyglyceryl-3 stearate, polyglyceryl-10 stearate, polyglyceryl-10 oleate, and polyglyceryl-10 caprylate/caprate, and mixtures thereof;
        the humectant comprises a polyol selected from the group consisting of glycerol, propylene glycol, polyglycerol, sorbitol, and mixtures thereof; and
        the emollient comprises an oil selected from the group consisting of an ester oil, an ether oil and mixtures thereof; and
        the emulsifier is present in an amount between 15% and 60% by weight, based on the weight of the composition;
        the humectant is present in an amount between 15% and 45% by weight, based on the weight of the composition; and
        the emollient is present in an amount between 15% and 60% by weight, based on the weight of the composition.

2. The concentrate composition according to claim 1, wherein
    (a) the emulsifier is present in an amount between 20% and 50% by weight, based on the weight of the composition;
    (b) the humectant is present in an amount between 20% and 40% by weight, based on the weight of the composition; and
    (c) the emollient is present in an amount between 20% and 55% by weight; based on the weight of the composition.

3. The concentrate composition according to claim 1, wherein the ester oil is a dialkyl carbonate.

4. The concentrate composition according to claim 3, wherein the dialkyl carbonate is dicaprylyl carbonate, ethylhexyl carbonate, dihexyl carbonate or a mixture thereof.

5. The concentrate composition according to claim 1, further comprising water and the water is present in an amount of less than 10% by weight, based on the weight of the composition.

6. The concentrate composition according to claim 1, wherein:
   (a) the emulsifier comprises polyglyceryl-10 oleate;
   (b) the humectant comprises glycerol; and
   (c) the emollient comprises a dicaprylyl carbonate.

7. A wet wipe impregnating formulation comprising
   (a) a concentrate composition according to claim 1, and
   (b) water, a lower alcohol or a mixture thereof.

8. The wet wipe impregnating formulation according to claim 7, wherein the formulation contains 0.1% to 50% by weight of the concentrate composition and from 99.9% to 50% by weight of water, a lower alcohol or a mixture thereof, based on the weight of the formulation.

9. The wet wipe impregnating formulation according to claim 8, wherein the formulation contains between 0.5% and 5% by weight of the concentrate composition, based on the weight of the formulation.

10. The wet wipe impregnating formulation according claim 7, further comprising an active pharmaceutical ingredient, an antimicrobial agent, a preservative, a fragrance or a mixture thereof.

11. A wet wipe comprising a wipe substrate and a wet wipe impregnating formulation according to claim 7.

12. The wet wipe according to claim 11, wherein the wipe comprises the wet wipe impregnating formulation and the wipe substrate in a weight ratio of 10:1 to 1:1.

13. The wet wipe according to claim 11, wherein the wipe substrate comprises woven or nonwoven material.

* * * * *